United States Patent
Gee et al.

(10) Patent No.: US 7,332,637 B2
(45) Date of Patent: Feb. 19, 2008

(54) ISOMERIZATION OF OLEFINS WITH CARBOXYLIC ACID

(75) Inventors: Jeffery C. Gee, Kingwood, TX (US); Willie J. Isom, Kingwood, TX (US); Bruce E. Kreischer, Humble, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 11/552,354

(22) Filed: Oct. 24, 2006

(65) Prior Publication Data

US 2007/0049784 A1 Mar. 1, 2007

Related U.S. Application Data

(62) Division of application No. 10/456,362, filed on Jun. 6, 2003.

(51) Int. Cl.
*C07C 5/23* (2006.01)
*C07C 5/27* (2006.01)
*B01J 31/04* (2006.01)

(52) U.S. Cl. .............. 585/664; 585/668; 585/671; 502/150

(58) Field of Classification Search ............. 585/664, 585/671, 668; 502/150
See application file for complete search history.

(56) References Cited

U.S. PATENT DOCUMENTS

| | | |
|---|---|---|
| 3,776,975 A | 12/1973 | Verbrugge et al. |
| 4,168,284 A | 9/1979 | Connor |
| 4,330,434 A | 5/1982 | Hughes |
| 4,672,147 A | 6/1987 | Farcasiu |
| 4,727,203 A | 2/1988 | Hamilton, Jr. |

(Continued)

FOREIGN PATENT DOCUMENTS

EP 0042537 12/1981

(Continued)

OTHER PUBLICATIONS

Foreign communication from a related counterpart application—International Search Report, PCT/US2004/015570, Nov. 24, 2004, 3 pages.

(Continued)

*Primary Examiner*—Glenn A. Caldarola
*Assistant Examiner*—In Suk Bullock
(74) *Attorney, Agent, or Firm*—Conley Rose, P.C.; Rodney B. Carroll

(57) ABSTRACT

A method of modifying the activity of a solid acid catalyst by contact with a carboxylic acid is presented. The modified catalyst is exposed to a feed mixture including olefins in a reaction zone, and an effluent including an isomerized olefin product is withdrawn from the reaction zone. The isomerized olefin product includes a more random distribution of internal olefins than the olefins of the feed mixture. The feed mixture and the isomerized olefin product include linear olefins. The isomerization results in no more than about 10 weight percent additional branched, compared to the olefins of the feed mixture, among the olefins of the isomerized olefin product. The isomerized olefin product includes no more than about 20 weight percent dimer. The olefin monomers of the feed mixture and the isomerized olefin product include from about 4 to about 30 carbon atoms. The effluent includes no more than about 20 weight percent ester. The solid acid catalyst may be an acidic ion exchange resin. The feed mixture may include olefins, esters, and carboxylic acid.

38 Claims, 1 Drawing Sheet

U.S. PATENT DOCUMENTS

| | | |
|---|---|---|
| 4,749,819 A | 6/1988 | Hamilton, Jr. |
| 5,008,466 A | 4/1991 | Schleppinghoff et al. |
| 5,237,120 A | 8/1993 | Haag et al. |
| 5,250,726 A | 10/1993 | Burke |
| 5,382,711 A | 1/1995 | Asaoka et al. |
| 5,426,199 A | 6/1995 | Lundquist |
| 5,545,792 A | 8/1996 | Cox |
| 5,589,442 A | 12/1996 | Gee et al. |
| 5,741,759 A | 4/1998 | Gee et al. |
| 5,849,974 A | 12/1998 | Clarembeau et al. |
| 5,948,946 A | 9/1999 | Harmer et al. |
| 5,965,783 A | 10/1999 | Gee et al. |
| 5,969,180 A | 10/1999 | Willems et al. |
| 6,054,629 A | 4/2000 | Baralt et al. |
| 6,100,223 A | 8/2000 | Gee |
| 6,191,076 B1 | 2/2001 | Gee |
| 6,281,404 B1 | 8/2001 | Miller |
| 6,315,964 B1 | 11/2001 | Knifton et al. |
| 6,355,855 B1 | 3/2002 | Nguyen et al. |
| 6,441,252 B1 | 8/2002 | Levin et al. |
| 6,465,697 B1 | 10/2002 | Palmer et al. |
| 6,576,801 B2 | 6/2003 | Smigelski, Jr. et al. |
| 6,653,513 B1 | 11/2003 | Iwahara |
| 2004/0249229 A1 | 12/2004 | Gee et al. |

FOREIGN PATENT DOCUMENTS

| | | |
|---|---|---|
| EP | 0 787 706 A1 | 8/1997 |
| WO | WO 96/19288 | 6/1996 |
| WO | WO 01/83409 A1 | 11/2001 |

OTHER PUBLICATIONS

Foreign communication from a related counterpart application—Written Opinion of the International Searching Authority, PCT/US2004/015570, Nov. 24, 2004, 4 pages.

Foreign communication from a related counterpart application—International Preliminary Report on Patentability, PCT/US2004/015570, Dec. 22, 2005, 6 pages.

ISOMERIZATION OF OLEFINS WITH CARBOXYLIC ACID

CROSS-REFERENCE TO RELATED APPLICATIONS

This is a Divisional Application of U.S. patent application Ser. No. 10/456,362, filed Jun. 6, 2003 and entitled "Isomerization of Olefins with Carboxylic Acid," which is hereby incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention relates generally to isomerization of olefins, and, more particularly, to modifying the activity of a solid acid catalyst with a carboxylic acid, exposing the modified catalyst to olefins, and producing an isomerized olefin product including a more random distribution of internal olefins where linearity, esterification, and dimerization are controlled.

BACKGROUND OF THE INVENTION

Various catalysts are known for their use in the double bond isomerization of olefins. However, many of these catalysts produce substantial amounts of polymer and/or skeletally isomerized product, i.e., branched olefins. For some applications, such as preparing internal olefins for alkylation reactions, it is desirable to limit branched products to the least amount possible, i.e, to maintain linearity between feed and product olefins. Therefore, for certain applications, it is desirable to use a catalyst that is selective for double-bond isomerization without skeletal isomerization.

Many processes for olefin isomerization require rigorous reaction conditions. Such conditions can cause hydrocarbon cracking and oligomerization, and require high energy consumption. Thus, in order to supply the commercial need for olefins and minimize production costs, a need exists for improved, more efficient, and less costly ways to isomerize olefins to linear internal olefins while minimizing dimerization, and without substantially increasing branched olefin content.

SUMMARY OF THE INVENTION

In an embodiment, a method of modifying the activity of a solid acid catalyst by contact with a carboxylic acid is presented. The modified catalyst is exposed to a feed mixture including olefins in a reaction zone, and an effluent including an isomerized olefin product is withdrawn from the reaction zone. The isomerized olefin product has a more random distribution of internal olefins than the olefins of the feed mixture. In an embodiment, the feed mixture and the isomerized olefin product include linear olefins. In another embodiment, the isomerization results in no more than about 10 weight percent additional branched olefins among the isomerized olefin products. In another embodiment, the isomerized olefin product includes no more than about 20 weight percent dimer. In another embodiment, the olefin monomers of the feed mixture and the isomerized olefin product include from about 4 to about 30 carbon atoms. In another embodiment, the effluent includes no more than about 20 weight percent ester. In an embodiment, the solid acid catalyst may be an acidic ion exchange resin. In an embodiment, the feed mixture includes olefins, esters, and carboxylic acid.

In an embodiment, an isomerization system is provided. The system includes a reaction zone, a solid acid catalyst, a carboxylic acid, and a feed having olefins. When the solid acid catalyst, carboxylic acid, and feed are present in the reaction zone, the system produces an effluent including an isomerized olefin product having a more random distribution of internal olefins than the olefins of the feed mixture. In an embodiment, the feed and the effluent include linear olefins. In another embodiment, the effluent includes isomers of esters. In another embodiment, the effluent includes a carboxylic acid. In another embodiment, the effluent includes olefin dimers. In another embodiment, the system includes a separation apparatus that receives the effluent and separates its components. In another embodiment, the system includes at least one recycle stream from the separation apparatus to the feed mixture. In an embodiment, the recycle stream includes a carboxylic acid. In another embodiment, the recycle stream includes isomers of esters.

DETAILED DESCRIPTION OF THE INVENTION

Figure 1:
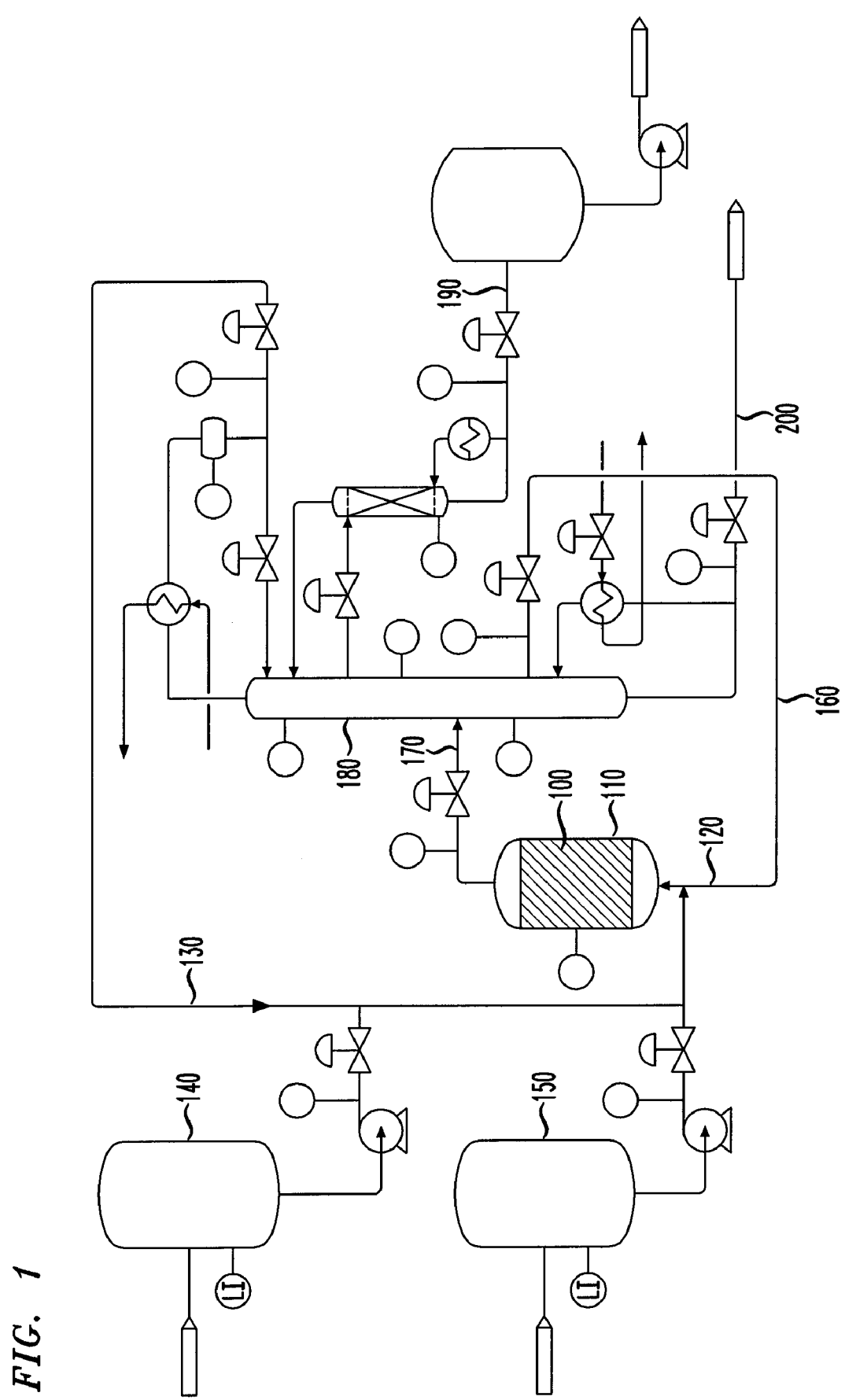
FIG. 1 illustrates an embodiment of an isomerization system in accordance with the present invention.

Systems and methods for isomerization of linear olefins are provided. Linear olefins are isomerized by a catalyst system including a solid acid catalyst and a carboxylic acid. The isomerization is accomplished with minimal added branching, minimal dimerization, and minimal esterification, while achieving a more random, and possibly a substantially thermodynamic, distribution of internal olefins.

In an embodiment, a method is provided that includes modifying the activity of a solid acid catalyst by contacting it with a carboxylic acid, exposing the modified catalyst within a reaction zone to a feed mixture including olefins, and withdrawing from the reaction zone an effluent that includes an isomerized olefin product. For a feed mixture including olefins having a non-random distribution of internal olefins, the modified catalyst produces an isomerized olefin product in which the distribution of internal olefins is more random than in the olefins of the feed mixture. In an embodiment, a substantially thermodynamic distribution of internal olefins is achieved. The olefins of the feed mixture may or may not include a high percentage of alpha-olefins. The isomerization herein isomerizes the olefins of the feed mixture to more randomly distribute the locations of the double bonds among the olefins. For example, if the olefins in a feed mixture are 90 weight percent alpha-olefins (i.e., a non-random olefin distribution), the olefins would undergo the isomerization provided herein to reach a more random distribution of internal olefins, i.e., the weight percentage of the alpha-olefin component of the mixture would decrease, and the weight percentage of internal olefins in the mixture would increase.

The catalyst system for isomerization of olefins described herein is made up of a solid acid catalyst and a carboxylic acid, or its equivalent. The solid acid catalyst may be one or more of the compounds from the class known as acidic ion exchange resins. Examples of commercially available catalysts of this type include Amberlyst, which is made by Rohm and Haas, Inc., Dowex, which is manufactured by Dow, Inc., and Nafion, which is manufactured by E.I. du Pont de Nemours and Company. In an embodiment, the solid acid catalyst is a sulfonated copolymer of styrene and divinyl benzene. In another embodiment, the sulfonated copolymer of styrene and divinyl benzene is a cross-linked copolymer having a macroreticular pore structure, and is substantially free of moisture. In another embodiment, the solid acid catalyst is substantially free of water. In another embodiment, the moisture content of the solid acid catalyst is less than about 1.5 weight percent. In another embodiment, the solid acid catalyst is a commercially known catalyst, such as Amberlyst-15, which is produced by Rohm and Haas. Amberlyst-15 is a styrene-divinylbenzene copolymer having pendant sulfonic acid groups. In an embodiment, the activity of the solid acid catalyst is modified by contact with a carboxylic acid to form a catalyst system. Olefins contacted with such a catalyst system may undergo isomerization to form an isomerized olefin product.

Without being limited by theory, it is believed that the carboxylic acid modifies the activity of the solid acid catalyst by adsorbing onto the surface of the catalyst to form the catalyst system for isomerization of olefins described herein. The carboxylic acid is desirably introduced to the solid acid catalyst in an amount sufficient to bind with many of the active sites on the solid acid catalyst. In an embodiment, the carboxylic acid is present in an amount sufficient to saturate substantially all of the active sites on the solid acid catalyst. The carboxylic acid may be any carboxylic acid suitable for modifying a solid acid catalyst and executing the isomerization of linear olefins described herein. In an embodiment, the carboxylic acid is selected from the group consisting of formic acid, acetic acid, propionic acid, butyric acid, pentanoic acid, hexanoic acid, octanoic acid, nonanoic acid, decanoic acid, carboxylic acids heavier than decanoic acid, and combinations thereof. In a desirable embodiment, the carboxylic acid is propionic acid. In another desirable embodiment, the carboxylic acid is acetic acid. The carboxylic acid may become a part of the catalyst system by addition, along with olefins, as a part of a feed mixture to the reaction zone described herein. In an alternative embodiment, the catalyst system is prepared by adding the carboxylic acid to the solid acid catalyst and then placing the catalyst system in the reaction zone. In another embodiment, the carboxylic acid is generated in situ. Examples of compounds capable of generating carboxylic acid in situ include esters and, if water is present, acid anhydrides. In an embodiment where at least some of the carboxylic acid is generated in situ, the carboxylic acid is introduced to the reaction zone via reverse esterification. In another embodiment, the carboxylic acid reactivates the solid acid catalyst by displacement of water. In yet another embodiment, contacting the solid acid catalyst with a carboxylic acid simultaneously removes water from the solid acid catalyst and saturates the active sites on the solid acid catalyst. Carboxylic acid is not consumed by the isomerization reaction described herein. Thus, once an appropriate level of carboxylic acid has been reached it is not necessary to add fresh carboxylic acid to the reactor. Rather, the carboxylic acid necessary to maintain the reaction may be obtained via recycling components of the reactor effluent, which includes carboxylic acid and/or a compound capable of generating a carboxylic acid under reaction conditions, such as an ester.

The feed mixture described herein is introduced to a reaction zone and includes linear olefins. In an embodiment, no more than about 10 weight percent of the olefins in the feed mixture include branching. The olefins of the feed mixture typically include a non-random distribution of internal olefins. In an embodiment, the olefins of the feed mixture may be made up primarily of alpha olefins. In another embodiment, the olefins of the feed mixture may be made up of at least 90 weight percent alpha olefins. The number of carbon atoms in the olefins of the feed mixture may be within a desired range. The olefins of the feed mixture should include a sufficient number of carbon atoms to exist in the liquid phase at the reaction temperature, or be convertible to olefins capable of existing in the liquid phase under reaction conditions. In an embodiment, the olefins in the feed mixture include one or more olefins having from about 4 to about 30 carbon atoms. In another embodiment, the olefins in the feed mixture include one or more olefins having from about 4 to about 20 carbon atoms. In another embodiment, the olefins in the feed mixture include one or more olefins having from about 16 to about 18 carbon atoms.

In addition to olefins, the feed mixture may include carboxylic acid and/or a compound capable of generating a carboxylic acid under the reaction conditions described herein. In an embodiment, the feed mixture includes no more than about 8 weight percent carboxylic acid. In another embodiment, the feed mixture includes no more than about 5 weight percent carboxylic acid. In another embodiment, the feed mixture includes no more than about 3 weight percent carboxylic acid. In another embodiment, the feed mixture includes no more than about 1 weight percent carboxylic acid. In another embodiment, the feed mixture includes linear olefins and isomers of esters of said linear olefins. In another embodiment, the feed mixture includes linear olefins, isomers of esters, and carboxylic acid. In another embodiment, the feed mixture includes components from one or more recycle streams.

The level of moisture (water) in the feed mixture may also be controlled. In an embodiment, the mixture includes no more than about 1000 parts per million by weight of water. In another embodiment, the mixture includes no more than about 500 parts per million by weight of water. In still another embodiment, the mixture includes no more than about 100 parts per million by weight of water.

The reaction zone herein may be defined by any reaction means known in the art that provides for contacting of the solid acid catalyst with the carboxylic acid, and/or exposure of the catalyst system to linear olefins under suitable reaction conditions to produce the effluent described herein. The reaction zone may be defined by a reactor vessel into which the feed mixture is introduced. The components of the feed mixture, which may include linear olefins, carboxylic acid, esters, and/or other carboxylic acid precursors, may be introduced separately into the reaction zone as separate feed streams, or they may be introduced together as a pre-combined mixture. Examples of reactors that are known in the art and that suitably provide for the isomerization described herein include fixed bed reactors, batch reactors, continuous flow reactors, and moving bed reactors, such as fluidized bed reactors and trickle bed reactors. In a desirable embodiment, the reaction zone is defined by a fixed bed reactor.

Controlled reaction zone conditions include weight hourly space velocity (whsv), reaction zone temperature, and pressure. In an embodiment, whsv is from about 0.1 to about 5.0. In another embodiment, whsv is from about 0.15 to about 3.0. In another embodiment, whsv is from about 0.2 to about 1.5. In an embodiment, reaction zone temperature is from about 20 to about 220 degrees Celcius. In another embodiment, reaction zone temperature is from about 50 to about 175 degrees Celcius. In another embodiment, reaction zone temperature is from about 100 to about 110 degrees Celsius. Reaction zone pressure is at least sufficient to keep the feed mixture, reaction zone contents, and effluent in the liquid phase.

The effluent of the reaction zone is generally a mixture of compounds, including an isomerized olefin product, isomers of esters, and carboxylic acid. The isomerized olefin product portion of the reactor effluent includes both isomerized olefin monomers and dimers. Carboxylic acid in the effluent may be recycled as a feed or part of a feed to the reaction zone. The solid acid catalyst modified by the carboxylic acid controls the amounts of dimers and esters in the effluent. In an embodiment, the effluent includes from about 85 to about 95 weight percent olefin monomers, from about 0 to about 10 weight percent olefin dimers, from about 0 to about 15 weight percent esters, and from about 0 to about 5 weight percent carboxylic acid.

The feed mixture does not typically contain dimers, but some dimers are generally formed by the present isomerization. In addition, even though olefin monomers in the feed mixture may be linear as described herein, dimerization generally results in olefin dimers that are branched. The fraction of olefin monomers in the feed mixture that is converted to dimers is equal to the fraction of dimers present in the isomerized olefin product. In an embodiment, the isomerized olefin product comprises no more than about 20 weight percent dimer. In another embodiment, the isomerized olefin product comprises no more than about 10 weight percent dimer. In another embodiment, the isomerized olefin product comprises no more than about 5 weight percent dimer. In another embodiment, the isomerized olefin product comprises no more than about 1 weight percent dimer.

In an embodiment, the esters formed by the reaction described herein are secondary esters formed by the reaction of a carboxylic acid with an olefin. For example, 1-octadecene may react with propionic acid to form 2-octadecyl propionate, 3-octadecyl propionate, 4-octadecyl propionate, 5-octadecyl propionate, 6-octadecyl propionate, 7-octadecyl propionate, 8-octadecyl propionate, and/or 9-octadecyl propionate. In an embodiment, the effluent comprises no more than about 20 weight percent ester. In another embodiment, the effluent comprises no more than about 12 weight percent ester. In another embodiment, the effluent comprises no more than about 8 weight percent ester. In another embodiment, the effluent comprises no more than about 3 weight percent ester.

The isomerization reaction described herein limits branching due to skeletal isomerization. For purposes of this application, any "additional branched olefins" describe branching added due to skeletal isomerization, not branching due to dimerization, i.e., references to "additional branched olefins" describe additional branching among olefins having the same number of carbon atoms as olefins in the feed. In an embodiment, relative to any branching present among the olefins of the feed mixture, the isomerization herein results in no more than about 10 weight percent additional branched olefins (excluding dimers) among the olefins of the isomerized olefin product. In another embodiment, relative to any branching present among the olefins of the feed mixture, the isomerization herein results in no more than about 5 weight percent additional branched olefins (excluding dimers) among the olefins of the isomerized olefin product. In another embodiment, relative to any branching present among the olefins of the feed mixture, the isomerization herein results in no more than about 3 weight percent additional branched olefins (excluding dimers) among the olefins of the isomerized olefin product.

In addition to controlling linearity, the isomerization reaction produces an isomerized olefin product having a more random distribution of internal olefins. In an embodiment, the locations of the double bonds among the olefins of the isomerized olefin product are more randomly distributed than among the olefins of the feed mixture. In another embodiment, the isomerization described herein produces an isomerized olefin product having a substantially thermodynamic distribution of olefins. The fraction of alpha-olefins in the isomerized olefin product is controlled in such a thermodynamic distribution. In an embodiment, a substantially thermodynamic distribution of olefins includes no more than about 6 weight percent alpha olefins. In another embodiment, a substantially thermodynamic distribution of olefins includes no more than about 1 weight percent alpha olefins.

In addition to low (i.e., no more than about 5 or 6 weight percent) alpha-olefin content, the amount of 2-alkenes in an olefin product is generally indicative of the randomness of the distribution of internal olefins. In an embodiment, a substantially thermodynamic distribution of internal olefins in an isomerized olefin product includes a weight percent 2-alkene content that is within about 4 weight percent of the result of the formula: $200/(C\#-3)$; where "C#" is defined as the number of carbon atoms in an isomerized olefin. Example calculations deriving the 2-alkene content from the above formula for olefins having from 6 to 30 carbon atoms, which should be indicative of a substantially thermodynamic distribution of internal olefins, predict that there should be from about 66 to about 71 weight percent 2-alkenes among olefins having 6 carbon atoms; from about 40 to about 44 weight percent 2-alkenes among olefins having 8 carbon atoms; from about 28 to about 33 weight percent 2-alkenes among olefins having 10 carbon atoms; from about 22 to about 26 weight percent 2-alkenes among olefins having 12 carbon atoms; from about 18 to about 22 weight percent 2-alkenes among olefins having 14 carbon atoms; from about 15 to about 19 weight percent 2-alkenes among olefins having 16 carbon atoms; from about 13 to about 17 weight percent 2-alkenes among olefins having 18 carbon atoms; from about 11 to about 16 weight percent 2-alkenes among olefins having 20 carbon atoms; from about 10 to about 15 weight percent 2-alkenes among olefins having 22 carbon atoms; from about 9 to about 14 weight percent 2-alkenes among olefins having 24 carbon atoms; from about 9 to about 13 weight percent 2-alkenes among olefins having 26 carbon atoms; from about 8 to about 12 weight percent 2-alkenes among olefins having 28 carbon atoms; and from about 7 to about 11 weight percent 2-alkenes among olefins having 30 carbon atoms. It will be understood by those skilled in the art that, if the feed mixture contains olefins of more than one carbon chain length, the mole percent of each olefin component in the mixture must be considered for the above calculation to provide the 2-alkene content indicative of a substantially thermodynamic distribution of internal olefins.

In an embodiment, an isomerization system is provided. The isomerization system includes a reaction zone, a solid acid catalyst, a carboxylic acid, and a feed having a non-random distribution of linear olefins. In the presence of the solid acid catalyst and the carboxylic acid, or its equivalent in the reaction zone, the olefins of the feed undergo an isomerization reaction. In an embodiment, the system produces an effluent that includes one or more of an isomerized olefin product, isomers of esters, dimers, and carboxylic acid. Relative to the olefins in the feed, the isomerized olefin product of the effluent includes a more random distribution of internal olefins that results from the isomerization in the reaction zone. In an embodiment, the feed to the system includes alpha olefins. In another embodiment, the isomerization system further includes a separation apparatus for separating the reactor effluent into its various component streams. In another embodiment, the isomerization system including the separation apparatus further includes at least one recycle stream to the reaction zone. In another embodiment, the at least one recycle stream includes a carboxylic acid. In another embodiment, the at least one recycle stream includes isomers of esters. In another embodiment, such esters are secondary esters.

A desirable embodiment of the isomerization system is illustrated by FIG. 1. In the embodiment of FIG. 1, a reactor 100 encloses a fixed bed of solid acid catalysts 110. Normal (i.e., linear) alpha olefins (NAO) 150 mix with a carboxylic acid (i.e., propionic acid) 140, a carboxylic acid recycle 130, and an ester recycle 160 to form the reactor feed 120. Esters undergo reverse esterification to generate carboxylic acid in the reactor 100. As described herein, the carboxylic acid modifies the activity of the solid acid catalysts in the fixed bed 110 to form a catalyst system for isomerization. The NAO in the reactor feed 120 undergoes an isomerization reaction when exposed to the catalyst system in the fixed bed 110. The reactor effluent 170 includes an isomerized olefin product, isomers of esters, and carboxylic acid. The effluent 170 enters a separation apparatus 180, which in this embodiment is a distillation column. The isomerized olefin monomer product 190 from the separation apparatus 180 includes a distribution of internal olefins that is more random than the distribution of internal olefins in the feed 120. In addition, a carboxylic acid recycle stream 130, an ester recycle stream 160, and a dimer stream 200 are separated by the apparatus 180.

Commercial applications of the isomerized olefin products described herein include employment as drilling fluids for drilling subterranean oil and gas wells, as well as other drilling fluid applications and drilling procedures. Other applications include employment as feedstocks or raw materials for the production of oil and fuel additives and in the making of alkenyl succinic anhydrides, which are used as paper sizing agents.

EXAMPLES

The following examples, 1 through 14, are merely representative of aspects of the present invention and, as one skilled in the art would recognize, the present invention may be practiced without many of the aspects illustrated by the examples. Data in the following examples that represent compositions of reaction mixtures and reactor products were determined by gas chromatography using a standard boiling point capillary column and flame ionization detector (GC/FID). Levels of residual alpha olefins in the reactor products were measured by FTIR (Fourier Transform Infra Red spectroscopy).

Example 1

In a glass reactor, a mixture of 24 g of 1-hexadecene and 12 g of Amberlyst 15 Dry was stirred under nitrogen at 100° C. After 40 minutes, the C16 olefin had thoroughly isomerized to a substantially random distribution of linear internal positional isomers. The level of linear 2-alkenes in the hexadecene had reached about 15%. The level of dimer in the olefin was 11 weight percent.

Example 2

In a glass reactor, a mixture of 12 g Amberlyst 15 Dry and 24 g of a solution of 6.5 weight percent propionic acid in 1-hexadecene was stirred under nitrogen at 110° C. After 5 hours, the C16 olefin had thoroughly isomerized to a more random distribution of linear internal positional isomers. The level of 2-hexadecenes among the C16 olefins initially rose and then dropped to 15-17%. The level of dimer in the olefin was 7 weight percent.

Example 3

In a glass reactor, a mixture of 12 g Amberlyst 15 Dry and 24 g of a solution of 10 weight percent propionic acid in 1-hexadecene was stirred under nitrogen at 110° C. After 4.5 hours, the C16 olefin had thoroughly isomerized to a more random distribution of linear internal positional isomers. The level of 2-hexadecenes among the C16 olefins initially rose and then dropped to 15-17%. The level of dimer in the olefin was 3.5 weight percent.

Example 4

In a glass reactor, a mixture of 12 g Amberlyst 15 Dry and 24 g of a solution of 15 weight percent propionic acid in 1-hexadecene was stirred under nitrogen at 110° C. After 4.5 hours, the C16 olefin had thoroughly isomerized to a substantially random distribution of linear internal positional isomers. The level of 2-hexadecenes among the C16 olefins initially rose and then dropped to 15-17%. The level of dimer in the olefin was 3.5 weight percent.

Example 5

A sample of 20 g of Amberlyst 15 Dry was immersed in glacial acetic acid and mixed for several minutes. The acid was decanted away, and a fresh aliquot of glacial acetic acid was used to cover the Amberlyst 15 a second time. After additional mixing, the acetic acid was decanted and discarded. The resin was then washed in 15 ml 1-hexadecene for several minutes, and the rinsings were decanted and discarded. The resin was repeatedly rinsed with 15-20 ml aliquots of 1-hexadecene, until the rinse solution was clear and homogeneous. Finally, 26 g of 1-hexadecene was added to the resin, and the mixture of resin and olefin was stirred under nitrogen at 110° C. After 1.5 hours, the level of 2-hexadecenes in the C16 olefins had increased to at least 37 weight percent and then dropped to 16-17 weight percent, indicating that the hexadecene had isomerized to a mixture of essentially random linear internal positional isomers. About 3.4 weight percent of the olefin had converted to dimers. The mixture contained 8 weight percent hexadecyl acetates, which are secondary esters.

Example 6

The liquid product from Example 5 was removed from the resin, and the resin was rinsed with 15 ml 1-hexadecene. The rinse solution was removed and discarded, and 25 ml 1-hexadecene was added to the resin. This mixture was heated and stirred under nitrogen at 110° C. for an hour. The mixture was then cooled to near room temperature, and the liquid mixture was decanted away. The resin was rinsed twice with 15 ml 1-hexadecene, and then 25 ml fresh 1-hexadecene was added back to the resin.

The mixture of resin and olefin was stirred under nitrogen at 110° C. After 15 minutes, the level of 2-hexadecenes in the C16 olefins had peaked and then dropped to 13 weight percent, while 16 weight percent of the C16 olefins had formed dimers. The mixture had 2 weight percent hexadecyl acetates (secondary esters). The results showed how exposure of the catalyst to olefin eventually resulted in loss of adsorbed acetic acid and an increase in the activity of the catalyst to the point that a high level of isomerization with low dimerization was no longer possible. The results also indicated that the 2-hexadecenes formed dimer more readily than did the other linear internal olefins. This was evident because the level of 2-hexadecene in the olefin dropped well below the thermodynamic level of about 15-17 weight percent.

Example 7

The resin from Example 6 was rinsed several times with propionic acid and then several times with 1-hexadecene. Then 25 ml of 1-hexadecene was added to the resin, and the resin and olefin were stirred under nitrogen at 110° C. After 1.1 hours, the level of 2-hexadecenes in the C16 olefins had increased to at least 30 weight percent and then dropped to about 16 weight percent, while 3 weight percent of the olefin had formed dimers. The total mixture contained about 16 weight percent hexadecyl propionates, which are secondary esters.

Example 8

The product from Example 7 was removed from the resin, and the resin was rinsed several times with 1-hexadecene. Then 25 ml of 1-hexadecene was added to the resin, and the resin and olefin were stirred under nitrogen at 110° C. After 30 minutes, the level of 2-hexadecenes in the C16 olefins had peaked and then dropped to about 15 weight percent, while 4 weight percent of the olefin had formed dimers. The total mixture contained about 8 weight percent hexadecyl propionates (secondary esters). The presence of the propionic acid had permitted the dimer level to remain below 5 weight percent, while still permitting thorough isomerization of the hexadecene.

Example 9

The product from Example 8 was removed from the resin, and the resin was rinsed several times with 1-hexadecene. Then 25 ml of 1-hexadecene was added to the resin, and the resin and olefin were stirred under nitrogen at 110° C. After 16 minutes, the level of 2-hexadecenes in the C16 olefins had peaked and then dropped to about 15 weight percent, while 12 weight percent of the olefin had formed dimers. The total mixture contained about 3 weight percent hexadecyl propionates. The catalyst no longer contained enough adsorbed propionic acid to keep the dimer level below 5 weight percent, while still permitting thorough isomerization of the hexadecene.

Example 10

The product from Example 9 was removed from the resin, and the resin was rinsed with 1-hexadecene. Then the resin was stirred with 25 ml of distilled water. The water was withdrawn, and the catalyst was rinsed three times with 15-20 ml 1-hexadecene. Then 25 ml 1-hexadecene was added to the resin, and the resin and olefin were heated and stirred at 110° C. The flask remained open to allow water to evaporate, until the mixture's temperature reached 110° C. After stirring at 110° C. for an hour, the olefin had negligible 2-hexadecenes. The water had essentially deactivated the catalyst.

Example 11

The product from Example 10 was removed from the resin, and the resin was rinsed several times with propionic acid. The resin was also stirred for 30 minutes at 110° C. with 25 ml propionic acid. The propionic acid was then withdrawn from the resin, and the resin was rinsed twice with 25 ml of 1-hexadecene. Then the resin was stirred with 25 ml 1-hexadecene under nitrogen at 110° C. After 4 hours, the level of 2-hexadecenes in the C16 olefins had increased to at least 48 weight percent and then dropped to 15-16 weight percent, while about 3 weight percent of the olefin had dimerized. The mixture contained about 15 weight percent hexadecyl propionates. The propionic acid treatment had restored the catalyst's activity.

Example 12

A fixed bed reactor packed with 72 grams of Amberlyst 15 Dry was assembled from a 0.75 inch ID stainless steel pipe heated inside an oven. The feed mixture contained 1-octadecene (97-98 weight percent) and propionic acid (2-3 weight percent). The unit operated continuously at 110° C. and a number of different whsv's (weight hourly space velocities) over a period of several weeks. Table 1, below, shows results of a number of samples obtained at different whsv's and at different ages of the catalyst. FTIR was the technique used to determine the residual alpha olefin in the C18 olefin stream. The weight percent 2-alkene refers to GC/FID results obtained by integrating the signal of only the C18 olefins. The weight percent dimers are the GC/FID results obtained by integrating only the C18 and C36 signals. The weight percent esters refer to the entire effluent mixture and are calculated from GC/FID data, after correction for non-hydrocarbon response factors. The level of propionic acid in the effluent held at 0-0.5 weight percent. Note that a whsv of about 0.4-0.5 was appropriate for producing olefin with a substantially random or substantially thermodynamic distribution of linear internal isomers, while a whsv of about 1 was appropriate for reducing the alpha content to about 3 weight percent and leaving many isomers with double bonds near the ends of the carbon chains. The C18 isomerized olefins (monomers) in the isomerized olefin product contained less than 4 weight percent additional branched olefins, relative to the C18 olefins in the feed mixture, as determined by GC/FID analysis of the hydrogenated products.

TABLE 1

Selected Data for Effluent from Fixed Bed Unit at 110° C.

| Days Online | WHSV | Weight % acid in feed | Mole % alpha olefin in olefin product | Weight % 2-alkene in olefin product | Weight % dimer in olefin product | Weight % ester in effluent |
|---|---|---|---|---|---|---|
| 17.10 | 0.39 | 2.8 | <1 | 15.0 | 2.8 | 8.9 |
| 39.30 | 0.16 | 2.0 | <1 | 14.3 | 1.4 | 7.2 |
| 45.02 | 1.04 | 1.9 | 3.0 | 36.4 | 0.5 | 7.3 |
| 53.10 | 1.96 | 1.9 | 35.0 | 43.4 | 0.0 | 7.0 |
| 55.02 | 2.88 | 1.9 | 61.0 | 36.3 | 0.0 | 5.7 |

Example 13

A second fixed bed reactor was constructed using 32.7 g Amberlyst 15 Dry and a 0.75 inch ID stainless steel pipe. Neat propionic acid was added to the resin, which was allowed to swell to its maximum volume. Neat propionic acid was then pumped over the resin for several hours, before the feed was switched to neat 1-octadecene. The C18 olefin was pumped over the resin at 110° C. and whsv=1. After one day, the C18 olefins in the effluent reached a substantially thermodynamic distribution of linear internal olefins as indicated by a 2-octadecene content of 13-14 weight percent in the C18 portion of the effluent. In addition, about 3 weight percent of the feed olefins formed dimers in the effluent, and about 6 weight percent propionic acid and about 22 weight percent octadecyl propionates (esters) were found in the effluent. After two days, the propionic acid level in the effluent had dropped to less than 0.5 weight percent, while about 15 weight percent of the C18 had dimerized, and about 5 weight percent of the effluent was octadecyl propionates.

The feed was switched from neat 1-octadecene to a mixture of 1.5 weight percent propionic acid and 98.5 weight percent C18 alpha olefins, and the temperature was lowered to 105° C. At whsv=1, the effluent contained C18 olefins that had achieved a substantially thermodynamic distribution of linear internal olefins (15 weight percent of the C18 was 2-octadecenes; <1 weight percent was 1-octadecene), and about 4 weight percent of the C18 olefins had formed dimer. The effluent contained about 5 weight percent octadecyl propionates and 0.2 weight percent propionic acid.

Similarly, with 1 weight percent propionic acid and 99 weight percent C18 alpha olefins in the feed, at 80° C. and whsv=1, the effluent contained C18 olefins having about 3-4 weight percent alpha olefins and 38 weight percent 2-octadecenes. About 2 weight percent of the C18 alpha olefins in the feed formed dimers. The percentages of alpha olefins and 2-alkenes indicate that a more random distribution of internal olefins was produced, but short of a substantially thermodynamic distribution.

Example 14

A hexadecene sample that was 70 weight percent 7- and 8-hexadecenes (30 weight percent was methyl pentadecenes) was combined with propionic acid so that propionic acid was 10 weight percent of the resulting solution. In a glass reactor, a mixture of 12 g Amberlyst 15 Dry and 24 g of the propionic acid/hexadecenes solution was stirred under nitrogen at 110° C. After 4 hours, the linear C16 olefins had thoroughly isomerized to a more random (in this case, substantially thermodynamic) distribution of linear internal olefins. Of the linear C16 olefins in the resultant mixture, about 14 weight percent were linear 2-hexadecenes. About 6 weight percent of the original olefin sample formed dimers, i.e., dimers made up about 6 weight percent of the olefin product.

While the present invention has been illustrated and described in terms of particular apparatus and methods of use, it is apparent that equivalent techniques and ingredients may be substituted for those shown, and other changes can be made within the scope of the present invention as defined by the appended claims.

The particular embodiments disclosed herein are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What we claim as our invention is:

1. A method comprising:
   modifying the activity of a solid acid catalyst by contact with a carboxylic acid;
   exposing the modified catalyst within a reaction zone to a feed mixture including olefins; and
   withdrawing from said reaction zone an isomerized olefin product,
   wherein said feed mixture comprises carboxylic acid, and wherein said carboxylic acid comprises no more than about 1 weight percent of said feed mixture.

2. The method of claim 1 wherein a location of the double bonds among the olefins of said isomerized olefin product are more randomly distributed than among the olefins of said feed mixture.

3. The method of claim 1 wherein said isomerized olefin product comprises a substantially thermodynamic distribution of internal olefins.

4. The method of claim 1 wherein said feed mixture comprises alpha-olefins.

5. The method of claim 1 wherein said feed mixture and said isomerized olefin product comprise linear olefins.

6. The method of claim 5 wherein said method results in less than about 10 weight percent additional branched olefins among the olefins of said isomerized olefin product.

7. The method of claim 5 wherein said method results in less than about 3 weight percent additional branched olefins among the olefins of said isomerized olefin product.

8. The method of claim 1 wherein an effluent from said reaction zone comprises from about 85 to about 95 weight percent olefin monomers, from about 0 to about 10 weight percent olefin dimers, from about 0 to about 15 weight percent esters, and from about 0 to about 5 weight percent carboxylic acid.

9. The method of claim 1 wherein said isomerized olefin product comprises no more than about 5 weight percent dimer.

10. The method of claim 1 wherein said olefins and said isomerized olefin product comprise one or more olefins having from about 4 to about 20 carbon atoms.

11. The method of claim 1 wherein said olefins and said isomerized olefin product comprise one or more olefins having from about 16 to about 18 carbon atoms.

12. The method of claim 1 wherein said isomerized olefin product comprises no more than about 5 weight percent alpha olefin.

13. The method of claim 1 wherein said isomerized olefin product comprises no more than about 1 weight percent alpha olefin.

14. The method of claim 1 wherein an effluent from said reaction zone comprises no more than about 8 weight percent ester.

15. The method of claim 1 wherein an effluent from said reaction zone comprises no more than about 3 weight percent ester.

16. The method of claim 1 wherein said solid acid catalyst comprises an acidic ion exchange resin.

17. The method of claim 1 wherein said solid acid catalyst comprises a sulfonated copolymer of styrene and divinylbenzene.

18. The method of claim 1 wherein said feed mixture comprises esters.

19. The method of claim 1 wherein said carboxylic acid is generated by a compound capable of generating a carboxylic acid under a plurality of conditions within the reaction zone.

20. The method of claim 19 wherein said carboxylic acid is generated from an acid anhydride.

21. The method of claim 19 wherein said carboxylic acid is generated from an ester via reverse esterification.

22. The method of claim 1 wherein said carboxylic acid is selected from the group consisting of formic acid, acetic acid, propionic acid, butyric acid, pentanoic acid, hexanoic acid, octanoic acid, nonanoic acid, decanoic acid, carboxylic acids heavier than decanoic acid, and combinations thereof.

23. The method of claim 1 wherein said carboxylic acid is acetic acid.

24. The method of claim 1 wherein said carboxylic acid is propionic acid.

25. The method of claim 1 wherein said solid acid catalyst is substantially free of water.

26. The method of claim 19 wherein said feed mixture comprises no more than about 1000 parts per million by weight of water.

27. The method of claim 19 wherein said feed mixture comprises no more than about 100 parts per million by weight of water.

28. A method of isomerizing olefins that increases the randomness of the distribution of internal olefins comprising:

modifying a solid acid catalyst by contact with a carboxylic acid; and exposing the modified catalyst to olefins within a reaction zone, wherein an effluent from the reaction zone comprises no more than about 5 weight percent dimers and no more than about 8 weight percent esters, and wherein the carboxylic acid comprises no more than about 3 weight percent of a feed mixture.

29. A method for isomerizing olefins, comprising:

contacting a solid acid catalyst with a plurality of olefins and a carboxylic acid, thereby producing an isomerized olefin product, wherein the carboxylic acid comprises no more than about 1 weight percent of a feed mixture.

30. The method of claim 29 wherein the olefins comprise alpha-olefins.

31. The method of claim 29 wherein the isomerized olefin product comprises no more than about 10 weight percent more branched olefins than is in the olefins.

32. The method of claim 29 wherein the isomerized olefin product comprises no more than about 5 weight percent dimer.

33. The method of claim 29 wherein the isomerized olefin product comprises no more than about 5 weight percent alpha olefin.

34. The method of claim 29 wherein the contacting produces no more than about 3 weight percent ester.

35. The method of claim 29 wherein the solid acid catalyst comprises an acidic ion exchange resin.

36. The method of claim 29 wherein the solid acid catalyst comprises a sulfonated copolymer of styrene and divinylbenzene.

37. The method of claim 29 wherein the carboxylic acid is generated by a compound capable of generating a carboxylic acid under a plurality of conditions within a reaction zone.

38. The method of claim 29 wherein the carboxylic acid is selected from the group consisting of formic acid, acetic acid, propionic acid, butyric acid, pentanoic acid, hexanoic acid, octanoic acid, nonanoic acid, decanoic acid, carboxylic acids heavier than decanoic acid, and combinations thereof.

* * * * *